(12) United States Patent
Caplan et al.

(10) Patent No.: US 7,262,299 B2
(45) Date of Patent: Aug. 28, 2007

(54) CATALYSTS

(75) Inventors: Neil Aubrey Caplan, Cambridge (GB); Frederick Ernest Hancock, Cleveland (GB)

(73) Assignee: Johnson Matthey PLC, London (GB)

( * ) Notice: Subject to any disclaimer, the term of this patent is extended or adjusted under 35 U.S.C. 154(b) by 429 days.

(21) Appl. No.: 10/495,004

(22) PCT Filed: Oct. 31, 2002

(86) PCT No.: PCT/GB02/04928

§ 371 (c)(1), (2), (4) Date: May 10, 2004

(87) PCT Pub. No.: WO03/039746

PCT Pub. Date: May 15, 2003

(65) Prior Publication Data

US 2005/0033100 A1    Feb. 10, 2005

(30) Foreign Application Priority Data

Nov. 9, 2001  (GB)  ................................. 0126935.6

(51) Int. Cl.
*C07D 221/02*  (2006.01)
*C07D 413/00*  (2006.01)

(52) U.S. Cl. ...................... 546/112; 548/229
(58) Field of Classification Search ................ 585/361; 546/112; 548/229

See application file for complete search history.

(56) References Cited

U.S. PATENT DOCUMENTS 3,444,253 A    5/1969  Reimlinger et al.
4,665,247 A    5/1987  Dessau
5,852,205 A   12/1998  Bethell et al.

OTHER PUBLICATIONS

David A. Evans et al., "Chiral Bis(oxazoline)copper(II) Complexes as Lewis Acid Catalysts for the Enantioselective Diels-Alder Reaction," *J. Am. Chem. Soc.*, vol. 121, No. 33, 1999, pp. 7559-7573.
D. A. Evans et al., Asymmetric Diels-Alder Cycloaddition Reactions with Chiral α,β-Unsaturated N-Acyloxazolidinones, *J. Am. Chem. Soc.*, vol. 110, No. 4, 1988, pp. 1238-1256.
D. A. Evans et al., "Bis(imine)-Copper(II) Complexes as Chiral Lewis Acid Catalysts for the Diels-Alder Reaction," *Tetrahedron Letters*, vol. 34, No. 44, 1993, pp. 7027-7030.
David A. Evans et al., "Dis(oxazoline)copper(II) Complexes as a Chiral Catalysts for the Enantioselective Diels-Alder Reaction," *J. Am. Chem. Soc.*, vol. 115, No. 14, 1993, pp. 6460-6461.
David A. Evans et al., "Bis(oxazline)-Copper Complexas as Chiral Catalysts for the Enantioselective Aziridination of Olefins," *J. Am. Chem. Soc.*, vol. 115, No. 12, 1993, pp. 5328-5329.
David A. Evans et al., "Enantioselective Synthesis of Bihydropyrans. Catalysis of Hetero Diels-Alder Reactions by Bis(oxazoline) Copper(II) Complexes," *J. Am. Chem. Soc.*, vol. 122, No. 8, 2000, pp. 1635-1649.
J. M. Fraile et al., "Bis(oxazoline)-metal complexes immobilised by electrostatic interactions as heterogeneous catalysts for enantioselective Diels-Alder reactions," *Journal of Molecular Catalysis A: Chemical*, vol. 165, Issues 1-2, Jan. 8, 2001, pp. 211-218.
Günter Helmchen et al., "$C_2$-Symmetric Bioxazolines and Bithiazolines as New Chiral Ligands for Metal Ion Catalyzed Asymmetric Syntheses: Asymmetric Hydrosilylation," *Synlett*, Apr. 1991, pp. 257-259.
Mogens Johannsen et al., Asymmetric Hetero Diels-Alder Reactions and Ene Reactions Catalyzed by Chiral Copper(II) Complexes, *J. Org. Chem.*, vol. 60, No. 18, 1995, pp. 5757-5762.
Karl Anker Jørgensen et al., "Catalytic Asymmetric Addition Reactions of Carbonyls. A Common Catalytic Approach," *Acc. Chem. Res.*, vol. 32, No. 7, 1999, pp. 605-613.
Christopher Langham et al., "Heterogeneous aziridination of alkenes using $Cu^{2+}$ exchanged zeolites," *Applied Catalysis A: General*, vol. 182, 1999, pp. 85-89.
Dieter Müller et al., $C_2$-Symmetric 4,4', 5,5'-Tetrahydrobi(oxazoles) and 4,4'5,5'-Tetrahydro-2,2'-methylenebis[oxazoles] as Chiral Ligands for Enantioselective Catalysis, *Helvetica Chimica Acta*, vol. 74, 1991, pp. 232-240.
Dalit Rechavi et al., "Heterogenization of a Chiral Bis(oxazoline) Catalyst by Grafting onto Silica," *Organic Letters*, vol. 3, No. 16, 2001, pp. 2493-2496.
International Search Report dated Feb. 4, 2003, from International Applicaiton No. PCT/GB02.04928.
Evans et al., "Catalytic Enantioselective Hetero Diels—Alder Reactions of α,β-Unsaturated Acyl Phosphonates with Enol Ethers," *J. Am. Chem. Soc.*, 1998, vol. 120, No. 19, pp. 4895-4896.

*Primary Examiner*—Glenn Caldarola
*Assistant Examiner*—In Suk Bullock
(74) *Attorney, Agent, or Firm*—RatnerPrestia

(57) ABSTRACT

A process for performing a catalytic Diels-Alder reaction by reacting a diene with a dienophile in the presence of a heterogeneous catalyst comprising a zeolitic material exchanged or impregnated with ions of a Lewis acidic metal is described. The catalyst, for example, copper-exchanged zeolite Y, may be treated with chiral bis(imine) compounds to direct the chirality of the reaction products. The catalyst can be separated from the reaction mixture and re-used in further Diels Alder reactions.

10 Claims, No Drawings

CATALYSTS

This application is the U.S. national phase application of PCT International Application No. PCT/GB02/04928, and claims priority of British Patent Application No. 0126935.6.

This invention relates to heterogeneous catalysts and in particular to the heterogeneous catalysis of Diels-Alder reactions. The products of such reactions are useful chemical intermediates or reagents for use in the production of fine chemicals or pharmaceutical intermediates.

Pioneered by two German chemists in 1950's, the Diels-Alder reaction is a reaction where a double (or triple) bond in a dienophile adds 1,4 to a conjugated diene. The inherent production of six-membered rings from acyclic materials makes it one of the most important reactions in organic synthesis. One form of the reaction is depicted below.

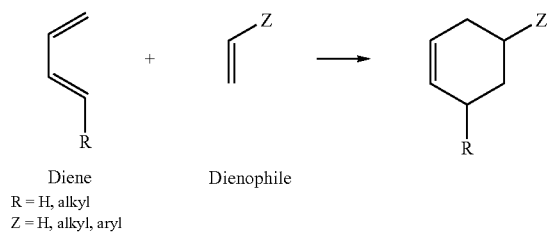

Diene      Dienophile
R = H, alkyl
Z = H, alkyl, aryl

A very wide rage of dienes and dienophiles have been reacted together to produce many new useful chemical compounds. Dienes may be substituted or unsubstituted, or may be cyclic, for example cyclopentadiene (Cp). In formal Diels-Alder reactions the dienophile is a compound containing a carbon-carbon double or triple bond, for example a vinyl or acetylenic compound, and the diene possesses two carbon-carbon double bonds, separated by a carbon-carbon single bond. Over the years since its discovery however the reaction has been extended to include non-carbon-carbon dienophiles, for example nitrile compounds, or alternatively, "dienes" in which a double bond links different heteroatoms; a so-called, "hetero"-Diels Alder reaction (HDA). Both formal- and hetero-Diels-Alder reactions are termed herein simply as "Diels-Alder reactions".

The Diels-Alder reaction may be made enantioselective by using a suitable diene and dienophile and placing an auxiliary on the diene or dienophile. By the term, "auxiliary" we mean a functional group containing optionally a chiral centre that may be present in the final product or removed or converted in a subsequent reaction, and which directs the chirality of the reaction product. Whilst an auxiliary may be present on the diene, it is often more convenient to synthesis a functional group on the dienophile. For example, the use of an imide derived from 2-oxazolidone (or its thioester) allows elevated enantiomeric excess (ee) values. (See for example, D. A. Evans et al, *J. Am. Chem. Soc.*, 1988, 110, 1238). A disadvantage with auxiliaries however is that they can alter the electronic properties of the diene or dienophile with the consequence that the reaction may become more difficult to control and predict in terms of rate, enantioselectivity and, where the diene is a cyclic compound such as cyclopentadiene, the endo:exo ratio. Endo and exo are terms used to designate the stereochemistry of bridged rings in a polycyclic structure. A group, e.g. an alkyl group, that is anti (i.e. opposite) to the longest bridge in the product structure is said to be exo; if it is syn (i.e. on the same side) it is endo. The Diels-Alder reaction occurs primarily in an endo rather than exo fashion when the reaction is kinetically controlled. It is preferred that the endo:exo ratio is high (>90:10) in enantioselective Diels-Alder reactions.

More conveniently, the Diels-Alder reaction may be made enantioselective by using a chirally-modified Lewis acid catalyst. This is generally achieved by complexing a Lewis-acidic metal with a homochiral ligand. A range of Lewis acidic metals and chiral ligands have been evaluated with different research groups favouring titanium, aluminium, boron, magnesium, iron, lanthanide or copper compounds. Chiral ligands include amino acids, bis(oxazoline), bis (naphthol) BINOL and tetra(aryldioxolanedimethanol) TADDOL compounds.

A group led by Evans in particular has concentrated on using Copper bis(oxazoline) compounds as homogeneous Lewis-acidic catalysts for Carbonyl-ene, Michael and Diels-Alder reactions. These catalysts are often formed in-situ by reaction of copper (II) trifluoromethanesulphonate or hexafluoroantimonate with a chiral bis(oxazoline). (See for example D. A. Evans et al, *J. Am. Chem. Soc.*, 1993, 115, 6460; *J. Am. Chem. Soc.*, 1999, 121, 7559; *Tet. Lett.*, 1993, 34 (44), 7027). The catalysts are chiral compounds possessing $C_2$-symmetry. Chirality is introduced by the configuration of the substituting groups on the oxazoline rings. These catalysts are found to catalyse the Diels-Alder reaction of cyclopentadiene with acrylamides. This reaction is depicted below;

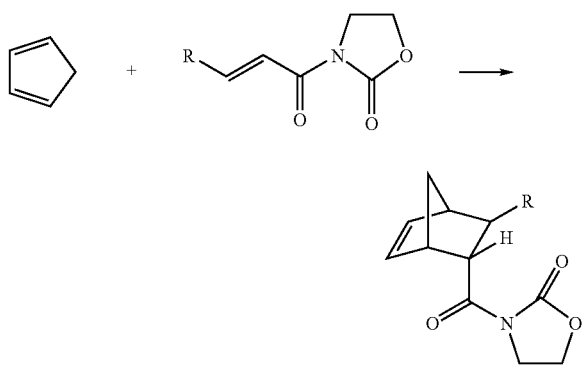

R = H, alkyl, aryl

The mechanism relies upon the ability of the substrate undergoing activation to chelate to the chiral cationic copper (II) catalyst. If a bis(oxazoline) ligand is present, the rigidity of the geometry forces one face of dienophile to be shielded by the bulky groups on the oxazoline and hence the ligand modified catalyst directs the chirality of the product. Thus the Diels-Alder reaction is sterically demanding and the geometry of the catalyst plays an important part in the enantiocontrol.

Homogeneous catalysts have also been found to be effective in the so-called 'hetero' Diels-Alder (HDA) reaction of dienophiles such as glyoxylate and pyruvate esters with electron-rich dienes. The nature of the dienophile depends on the reactivity or otherwise of the diene, for instance ketones are less reactive than aldehydes. Lewis acidic compounds based on Al, B, lanthanides, Ti, Cr, Mn, Rh and Cu have been used successfully. However, Jorgensen (K. A. Jorgensen, *J. Org. Chem.*, 1995, 60, 5757 and *Acc. Chem. Res.*, 1999, 32, 605) has found copper (II) bis(oxazolines) to be the best, most readily available catalysts for this chemistry. The HDA reaction can be extended to systems using electron-poor dienes and electron-rich dienophiles—the so-called electron inverse-demand HDA reaction. The catalytic enantioselective inverse-demand HDA reaction has been exemplified by Evans (D. A. Evans, *J. Am. Chem. Soc.,* 2000, 122, 1635), again using copper (II) bisoxazoline ligands to give high yields and enantioselectivities.

Nevertheless, such homogeneous catalysts and the processes using them remain limited in their economic efficiency because of the inability to readily remove the catalysts from the reaction medium. Costly solvent extraction techniques are used and concern over the environmental burden of the resulting catalyst waste and the general inability to re-use the separated catalyst make it desirable to employ a heterogeneous catalyst.

Recently workers have attempted to heterogenise a specific chiral bis(oxazoline) ligand on an inorganic silica and use a resulting Cu-containing catalyst for the Diels-Alder reaction (see D. Rechavi and M. Lemaire, *Org. Lett.,* 2001, 3 (16), 2493-6). Immobilisation of the ligand was achieved by a complex synthetic method that chemically modified the ligand to enable it to react with an organofunctional silane that was then used to provide a covalent link to the inorganic silica. The covalently anchored ligand was then reacted with copper compounds to provide the catalysts. Poor results were obtained when $Cu(OTf)_2$ (where OTf=trifluoromethanesulphonate) was used as the copper source, although better results were obtained with $Cu(ClO_4)$ $6H_2O$ in combination with a pretreatment of the ligand-modified silica with trimethylsilyl-groups. Although the latter catalyst was effective, the complicated and costly catalyst synthesis makes this approach less desirable.

Mayoral et al have recently reported (in *J. Mol. Catal. A: Chem.,* 2001, 165, 211) an attempt to use non-covalently bound chiral bis(oxazoline) ligands in the Diels-Alder reaction. Cu, Mg or Zn bis(axazoline) compounds were ion-exchanged into Laponite clay and Nafion silica resins and used in the reaction depicted above (where R=H, i.e. the reaction between cyclopentadiene and 3-(2-propenoyl)-2-oxazolidinone). However the results were poor and none of the enantioselectivities were above 11%. This may due to the demanding stereochemistry of the Diels-Alder reaction.

In U.S. Pat. No. 5,852,205, a metal-exchanged acidic zeolitic material, for example copper-exchanged zeolite Y, is described that may be used for the effective heterogeneous catalysis of the reaction between alkenes and nitrene donors to form aziridines. Furthermore, chiral aziridines could be prepared using these catalysts in combination with chiral bis(oxazoline) modifiers (see also P. McMorn et al, *Appl. Cat. A.,* 1999, 182, 85).

We have now found surprisingly that the usefulness of certain of the metal-exchanged zeolitic catalysts described for aziridination reactions may be extended to the more stereochemically demanding Diels-Alder reactions.

Accordingly the invention provides a process for performing a catalytic Diels-Alder reaction by reacting a diene with a dienophile in the presence of a heterogeneous catalyst comprising a zeolitic material exchanged or impregnated with ions of a Lewis acidic metal.

The zeolite employed may be selected depending on the nature of the reactants and the reaction product. The zeolite may be selected from the group of structures with at least 10 ring apertures such as DAC, EPI, EUO, FER, HEU, LAU, MEL, MFI, MFS, MTT, NES, NU-85, NU-86 and NU88, STI, TON, WEI, -PAR and -WEN and structures with 12-ring apertures such as *BEA, BOG, CAN, EMT, FAU, GME, LTL, MAZ, MEI, MOR, MTW, OFF and -RON.

Other zeolitic materials of use include phosphate materials such as MeALPO and SAPO, and zeolitic titanosilicates, vanadosilicates, ferrisilicates and borosilicates. Full details of many of these structures may be found in the "*Atlas of Zeolite Structure Types*", W. M. Meier and D. H. Olson, 3$^{rd}$ Revised Edition, 1992, Butterworth-Heinemann. It will be readily understood by those skilled in the art that zeolite structures may possess a range of framework compositions. The composition of the zeolite for the purposes of the present invention should be such that it possesses cation-exchangeable sites within the framework so that in the final catalyst at least some of the exchangeable cation sites are occupied by Lewis acidic metal ions. For example this may be achieved using aluminosilicate zeolites having a silica:alumina ratio of at least 1:2, more preferably 1:5. Although higher silica:alumina ratios can be used, the reduction in exchangeable sites (associated with aluminium in the framework) means that very high silica:alumina ratios are less preferred. Rather, if it is desired to reduce the number of acid sites in the zeolite, the zeolite may be treated with an alkali metal compound, e.g. sodium hydroxide. The preferred zeolite structures are FAU and MFI. The FAU zeolite structure corresponds to zeolite X and zeolite Y whereas the aluminosilicate MFI structure corresponds to ZSM-5. The preferred zeolites are zeolite Y and ZSM-5.

The catalyst of the present invention is a zeolite in which at least some of the exchangeable cation sites are occupied by Lewis acidic metal ions. Preferably, between 1 and 100% of the exchange sites occupied by Lewis acidic metal ions, preferably 10-80%, most preferably 25-75%. The exchanged catalyst may therefore contain between 0.1 and 15% by weight, preferably 0.5 to 7% by weight and most preferably 1 to 5% by weight of Lewis acidic metal.

The Lewis acidic metal ions comprise at least one Lewis acidic metal selected from Groups IIA, IVB, VB, VIB, VIII, IB, IIB or IIIA of the Periodic Table (as set out in the UK Abridgements of Patent Specifications for the Series 1525001 to 1537580). Preferred metals are Mg, Ti, V, Cr, Fe, Cu, Zn or Al. The most preferred metal is Cu (copper) and the most preferred catalysts are copper-exchanged zeolite Y and copper-exchanged ZSM-5.

The catalyst may be made directly from the zeolite using wet impregnation techniques in the pH range 4 to 8, preferably 5 to 7.5 and most preferably 5 to 6.5. Alternatively, dry impregnation of metal ions into the zeolite may be used, for example by dry-blending followed by a heat treatment, e.g. a protonated zeolite may be dry-blended with a Lewis acidic metal compound having a suitably volatile or readily removable anion, e.g. acetate or oxalate so that when the treated zeolite is heated, the Lewis acidic metal ion (cation) exchanges releasing the volatile compound.

It shall be understood by those skilled in the art that a portion of the cationic Lewis acidic metal ions will be exchanged following treatment but that a portion may remain un-exchanged but trapped within the zeolite cage structure. Where such metal ions are trapped within the zeolite cage structure, the zeolite may be described as impregnated. Thus the catalyst will comprise a zeolitic material exchanged or impregnated with ions of a Lewis acidic metal. The exchange/impregnation process may be carried out once, or repeated to obtain the desired metal loading. In wet impregnation, sources of the metal are typically aqueous solutions of salts such as the nitrate, sulphate or carboxylates such as the acetate, oxalate or citrate. For example, for copper, suitable salts are copper nitrate, copper oxalate and copper acetate. The exchanged/impregnated zeolite is then separated by filtration or by centrifuging, and may be washed to remove any unbound metal ions, and dried. Before use, the exchanged zeolite may, if desired, be calcined to remove counter ions, e.g. acetate, not removed by washing.

Herein, drying refers to a process where absorbed solvent, e.g. water, is driven off by heating at temperatures up to about 170° C., and calcining refers to a process where organic residues on the catalyst are destroyed by heating to temperatures above their decomposition temperature, for example 350-600° C.

The catalyst may be in any form readily used for the process, i.e. as a powder, granules, pellets or extrudates. These may be prepared by techniques known to those skilled in the art, including pelletising, extruding and spray-drying. The exchange/impregnation process may be performed on pellets or granules before, during or after forming using such techniques.

Whereas the catalyst of the present invention may be used to catalyse Diels-Alder reactions, the products of said reactions where chiral products are generated, comprise a racemic mixture. We have found that, surprisingly, enantioselective Diels-Alder reactions may be effected in the present invention when the metal-exchanged zeolitic material is subjected to a reaction with a chiral bis(imine) compound, in particular a chiral bis(imine) compound of formula (I) or formula (II);

$$n(R_2C) \underset{R^1}{\overset{X}{\underset{N}{\bigvee}}} \overset{Z}{\underset{N}{\bigvee}} \underset{R^2}{\overset{Y}{\bigvee}} (CR_2)n \quad (I)$$

$$n(R_2C) \underset{X-N}{\overset{R^1}{\bigvee}} \overset{Z}{\underset{N-Y}{\bigvee}} \underset{}{\overset{R^2}{\bigvee}} (CR_2)n \quad (II)$$

in which R may be hydrogen or alkyl (branched or linear C1-C10), $R^1$ and $R^2$ may be independently alkyl (branched or linear C1-C10), cycloalkyl, aryl or benzyl which may be substituted or unsubstituted; substituting groups being selected from a list comprising halogen, hydroxyl, carboxyl, amide, silyl and aryl; n is independently 1 or 2; X and Y are independently O, S, $CR_2$ or NR' (in which R' may be hydrogen, alkyl (branched or linear C1-C10), or an electron withdrawing group, e.g. $CO_2Et$); and Z is a linking group that links the carbons of the imine groups via between 0 and 3 linking atoms. For example Z may be of formula NR" or $CR''_2$ in which R" is independently hydrogen or alkyl, (branched or linear C1-C10) through which the imine groups are linked via the N and C atoms respectively, or pyridine, linked via the carbon atoms adjacent to the nitrogen atom of the pyridine ring. Furthermore, at least two of R, R', R", $R^1$ and $R^2$ may be linked so as to form at least one ring in the bis(imine) structure. En-amine compounds that are capable of forming imine compounds according to formula (I) or formula (II) are also necessarily included in the present invention.

To direct the chirality of the reaction products, preferably the bis(imine) possesses $C_2$-symmetry. Accordingly the bis(imine) may possess an axis of symmetry through Z and has $R_1$ and $R_2$ the same; n the same for both imine rings and the same X and Y groups. R is preferably hydrogen; $R^1$ and $R^2$ are preferably tert-butyl ($C(CH_3)_3$), iso-propyl ($CH(CH_3)_2$), phenyl ($C_6H_5$) or benzyl ($CH_2C_6H_5$); n is 1; X and Y are O and Z is $CH_2$, $C(CH_3)_2$, $NCH_3$ or 1,5-$C_5H_5N$. Accordingly, suitable bis(imine) compounds include, but are not restricted to the following, where $R^1$ and $R^2$ are as hereinbefore defined.

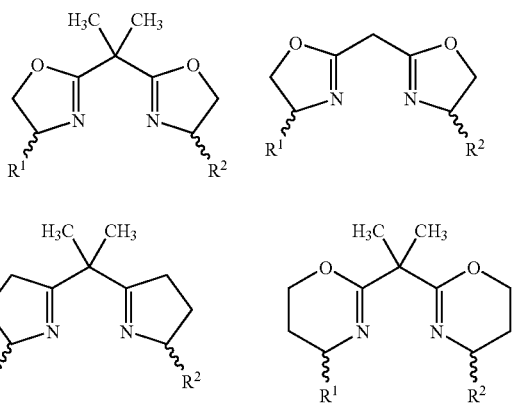

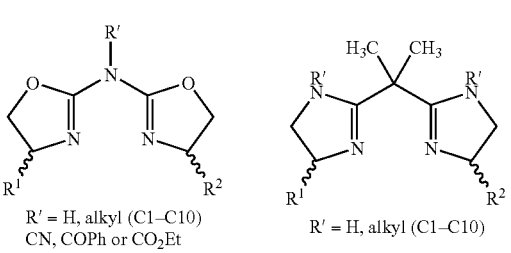

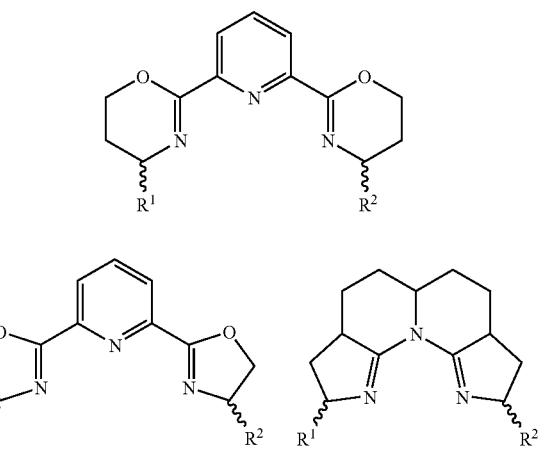

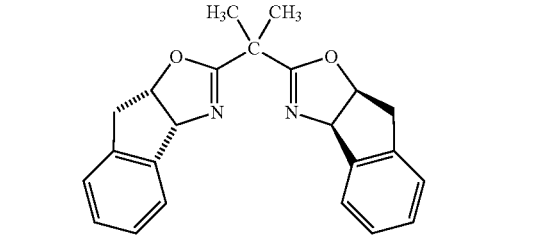

-continued

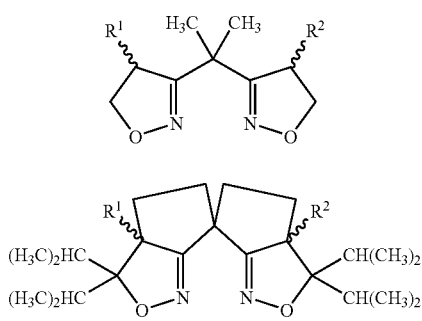

The chiral bis(imine) compounds have $R^1$ and $R^2$ bonded to chiral centres. The designations "(S,S)", and "(R,R)" describe the chiral configuration of the $R^1$ and $R^2$ groups within the bis(imine) structure.

Preferred bis(imines) include chiral bis(oxazolines), dis-ubstituted iso-oxazolines, symmetrical semicorrins and aza-semicorrins. Particularly preferred bis(imines) are chiral bis(oxazolines), especially disubstituted bis(oxazolines). Suitable chiral disubstituted bis(oxazolines) include (S,S)-bis(tert-butyloxazolines), (R,R)-bis(phenyloxazolines), (S,S)-bis(phenyloxazolines) and (R,R)-bis(benzyloxazolines). For example, with $Z=C(CH_3)_2$, and $R^1$ & $R^2$=tert-butyl, the bis(imine) compound is 2,2'-isopropylidenebis[4 (S)-4-tert-butyl-2-oxazoline]; with $Z=CH_2$, the bis(imine) is 2,2'-methylenebis[4(S)-4-tert-butyl-2-oxazoline]. A further preferred bis(oxazoline) is 2,2-bis(8,8'-dihydro-3aH-indeno[1,2-d]oxazol-2-yl)propane. Suitable chiral bis(oxazolines) may be readily synthesized using methods known to those in the art, for example using methods described in Pfalz et al, *Helv. Chim. Acta.*, 1991, 74, 232-240 and G. Helmchen et al., *Synlett*, 1991, 257-259, or are commercially available.

We have found that, where a bis(imine) is used with the catalyst of the present invention, the amount of bis(imine), for example bis(oxazoline), that may be used may be considerably less than with the analogous homogeneous catalyst. Thus whereas it is usual in homogeneous catalysis to use one or more moles of bis(oxazoline) per gram atom of the catalytic metal, in the present invention if more than one mole of bis(oxazoline) is used per gram atom of catalytic metal, the yields of desired product may be decreased, possibly as a result of the excess of bis(oxazoline) blocking the zeolite supercage structure. We prefer to employ not more than one equivalent of bis(imine) per Lewis acidic metal ion within the zeolite structure and most preferably between 0.40 and 0.80 molar equivalents of bis(imine) per Lewis acidic metal ion within the zeolite structure.

The treatment of the metal-exchanged zeolite with bis (imine) compound, if desired, may conveniently be performed separately from the process of the present invention or immediately before use. The generation of the treated catalyst may be carried out in diene, dienophile or another suitable medium. For example, where the diene or dienophile are liquid under the reaction conditions, it may be possible to disperse the metal-exchanged zeolite in one, add the bis(imine) compound, allow sufficient time for the reaction between metal and ligand to occur and then add the second reactant. Alternatively, the metal-exchanged zeolite catalyst may be treated with bis(imine) compound in the presence of a suitable solvent for the reaction before addition of the diene and dienophile. In a typical method for treating the catalyst with bis(imine) compound, pre-dried metal-exchanged zeolite is dispersed in a solvent and the bis(imine) compound added and stirred for sufficient time, e.g. 2-3 hours, for the bis(imine) compound to complex with the Lewis acidic metal. The treated catalyst may be recovered from the solvent, e.g. by filtration, and used separately, or, for example, the diene and dienophile may be added to the treated catalyst in-situ.

The dienes suitable for use in the process of the present invention may vary considerably depending upon whether the reaction is a formal Diels-Alder reaction, a hetero Diels-Alder reaction or an inverse electron demand hetero Diels-Alder reaction. By the term "diene" we include molecules having at least two double bonds and where the double bonds may or may not be between two carbon atoms. For example, suitable dienes include vinyl-phosphate, -sulponate and -carbonyl compounds. Useful dienes are depicted below.

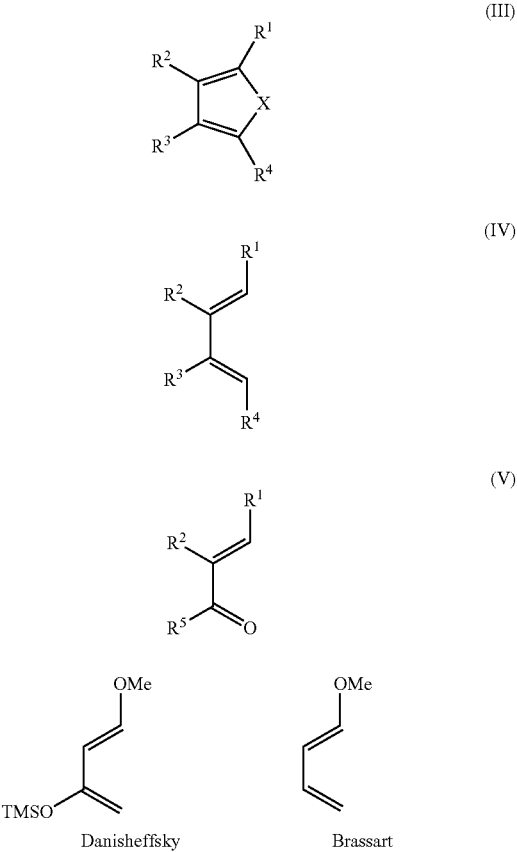

In (III) to (V) above, $R^1$, $R^2$, $R^3$ and $R^4$ may be independently hydrogen, substituted or unsubstituted alkyl or cycloalkyl (C1-C12) and aryl, alkoxy (C1-C12), siloxy (C1-C12), halide, amino, amido, nitrile, thiol, sulphide, carbonyl, sulphonyl or phosphonyl. Examples of suitable R-groups include methyl, ethyl, isopropyl, phenyl, substituted phenyl, methoxy, ethoxy, ethoxy-ethoxide, amino, dimethylamino, acetonyl, benzoyl and trimethylsilyl (TMSO). Substituting groups may be selected from the group comprising alkyl, aryl, halide, alkoxy, amido, amino, nitrile, carbonyl and sulphonyl. In cyclic diene (III), 'X' comprises $CH_2$, $C_2H_4$, $C_3H_6$ or a heteroatom selected from O, N (including N=N), S or P, which may be further substituted with, for example, hydrogen or a substituted or unsubstituted alkyl (C1-C12) or aryl group. Alternatively, the cyclic diene may comprise a heterocyclic molecule having greater than one heteroatom selected from O, N or S in the ring structure. For hetero Diels-Alder reactions using 'dienes' of formula (V), $R^5$ may be carbonyl, e.g. $CO_2Et$, or sulphonyl, e.g. $SO_2Ph$ (where Ph=phenyl) or phosphonyl, e.g. $P(O)(OCH_3)_2$. Particularly useful dienes include cyclopentadiene and substituted cyclopentadienes, furans, pyrroles, oxazoles and thiophenes, and the Danishefsky and Brassart dienes.

The dienophiles suitable for use in the process of the present invention may also vary considerably depending upon whether the reaction is a formal Diels-Alder reaction, a hetero Diels-Alder reaction or an inverse electron demand hetero Diels-Alder reaction. Useful dienophiles are depicted below.

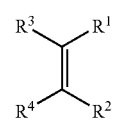
(VI)

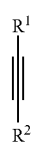
(VII)

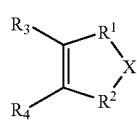
(VIII)

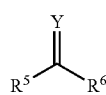
(IX)

In (VI), (VII), (VIII) and (IX) above $R^1$, $R^2$, $R^3$ and $R^4$ may be independently selected from hydrogen, substituted or unsubstituted alkyl or cycloalkyl (C1-C12) and aryl, alkoxy (C1-C12), siloxy (C1-C12), halide, amino, amido, nitrile, thiol, sulphide, carbonyl, eg in ketone, aldehyde, ester or carboxylic acid, nitro, sulphonyl or phosphonyl. Alternatively, $R^1$ and $R^2$ may be linked as in (VIII) via X. X comprises an alkyl group (C1-12, preferably C1-3) or a heteroatom selected from O, N (including N=N), S or P. For example the dienophile may be an anhydride where $R^1=R^2=CO$ and X=O, or other cyclic structure, e.g. where $R^1=R^2=NH$, X=CO; or $R^1=R^2=S$ and X=CO. In hetero Diels-Alder reactions dienophiles as depicted in (IX) in which Y may be O or NR (and R is hydrogen, alkyl or aryl) may be used. Preferably Y is O. Here $R^5$ and $R^6$ may be independently hydrogen, alkyl or cycloalkyl (C1-12), aryl, substituted aryl, ketone, aldehyde, ester, amide carboxylic acid, nitrile, nitrate, sulphonate or phosphonate. Preferably $R^5=R^6=CO_2R'$ (where R' is C1-C12 alkyl). Alternatively, the dienophile may be an unsaturated cyclic ether or an allene. Particularly useful dienophiles include maleic anhydride, substituted or unsubstituted acetylenes, acrylamides or quinones, phenylvinylsulphone, phenylvinylsulphoxide, acrylonitrile or acrolein, e.g. diethylacetylenedicarboxylate and diester carbonates.

It may also be possible to have the diene and dienophile present in the same molecule. For example in (VI) above, where $R^1=H$; $R^4=H$; $R^2=CO_2Et$ and $R^3=C_2H_4$-cyclo $(CHCH=CHCH=CHCH_2)$.

It will be understood by those skilled in the art that selection of certain substituents on the diene or dienophile may provide functional groups in the resulting molecule suitable for subsequent chemical transformation.

Valuable reaction products formed by or derivable from the process of the present invention include for example chiral cyclohexenes, cyclohexanones, cyclohexenones, cyclohexene carboxylic acids and amides, carbocycles, carbohydrates, lactones, dihydropyrans and derived tetrahydropyrans.

The molar ratio of diene to dienophile may be 1:1 however an excess of diene relative to dienophile improves the yields of product from the reactions. For example diene to dienophile ratios of between 1:1 and 10:1 and preferably 2:1 to 6:1 may be used in the present process. Alternatively an excess of dienophile may similarly be used to increase yield and enantioselectivity.

Solvents are preferably used in the process of the present invention. The solvents may be polar or non-polar. Examples include aromatic hydrocarbons such as toluene, xylene or mesitylene, halocarbons such as dichloromethane or chloroform, ethers such as diethyl ether or tetrahydrofuran. Preferably, the solvent is a polar solvent and most preferably, the solvent is dichloromethane. Strongly coordinating solvents such as acetonitrile are less preferred.

The reaction temperature employed in the process depends upon the nature, i.e. boiling point or stability, of the solvent and reactants or products but is generally in the range −80° C. to +80° C., with low temperatures, <40° C. preferred for enantiomeric Diels-Alder reactions. By cooling the reaction, the enantiomeric excess may be increased and in one preferred embodiment, the reaction is carried out at −80 to −60° C.

The process may be effected at any suitable pressure, e.g. atmospheric, although where the diene, dienophile or the reaction product is volatile or gaseous at the reaction temperature, the reaction pressure should preferably be sufficient to maintain them in the liquid state e.g. in solution.

The process of the present invention may be effected batch-wise or continuously. In a batch reaction, to obtain a useful reaction rate, the amount of catalyst employed is preferably such that there are about 0.01 to 0.5 molar equivalents and more preferably 0.02 to 0.25 molar equivalents of Lewis acidic metal per mole of dienophile.

An advantage of the catalysts of the present invention is that they may readily be separated from the reaction mixture and, if desired, re-used for subsequent reactions. The catalysts may be separated by known methods such as filtration or centrifugation. To remove undesirable residues of the reaction mixture from the catalyst, it may be advantageous to wash the catalyst using a suitable solvent for said undesirable residues and dry prior to re-use. Suitable solvents include aliphatic hydrocarbons such as hexane or heptane, aromatic hydrocarbons such as toluene, xylene or mesitylene, halocarbons such as dichloromethane or chloroform, ethers such as diethyl ether and esters such as ethyl acetate. The separated catalyst is preferably washed with ethyl acetate and dried under vacuum to remove traces of solvent and/or any traces of the reaction mixture prior to re-use. Preferable drying temperatures are in the range 20 to 160° C.

in air, nitrogen or under vacuum for between 1 and 24 hours. Additionally, if it is desired to remove a bis(imine) compound on the metal-exchanged zeolite, the catalyst may be calcined at temperatures of, e.g. 550° C. for e.g. 6 hours to completely destroy any organic residues.

and the crude product purified by flash column chromatography to yield the product, following solvent removal, as a white solid. The enantiomeric excess was determined using standard chiral HPLC techniques. The results are depicted in Table 1 below;

TABLE 1

| Example | Diene | Dienophile | Product | Time (hrs) | Yield (%) | Ee (%) |
|---|---|---|---|---|---|---|
| 2 | | | | 3 | 84 | 68 |

The invention is further illustrated by the following examples.

EXAMPLE 1

Preparation of a Copper Exchanged Zeolite Y

A 150 ml solution of copper (II) acetate (7.85 g, 39.3 mmol) was prepared using de-ionised water and buffered to approximately pH 6.5 using aqueous ammonia solution (35% wt). A commercially available Zeolite HY (50 g) was then added to the solution and the resulting suspension stirred at room temperature (ca 20° C.). The pH was monitored after 5 minutes and at 1, 2 and 5 hours and adjusted back to 6.5 where necessary with aqueous ammonia solution. The suspension was stirred for 16 hours then the exchanged zeolite was recovered by filtration and washed with de-ionised water. The exchanged zeolite was then dried at 110° C. followed by calcination at 550° C. for 6 hours. The copper loading of the resultant powder was measured by Inductively Coupled Plasma Atomic Absorption Spectroscopy (ICPAAS) at 3.1% by weight.

EXAMPLE 2

Heterogeneously Catalysed Acrylamide-Cyclopentadiene Reaction

Solvent-damp copper-exchanged zeolite Y (0.41 g, 85%, 0.17 mmol Cu) as prepared in Example 1 was placed in a Schlenk flask and dried under a high vacuum at about 150° C. for 2 hours. The flask was allowed to cool under nitrogen to room temperature (ca 20° C.). To the cool solid were added DCM (4.0 ml) and bis(imine) compound {2,2'-isopropylidene bis[4(S)-4-$^t$Butyl-2-oxazoline]} (0.025 g, 0.075 mmol). The suspension was stirred for 2 hours at room temperature (ca 20° C.) and then cooled to −78° C. Acrylimide(3-(2-propenoyl)-2-oxazolidinone) (0.24 g, 1.70 mmol) dissolved in DCM (1 ml) was added to the suspension and stirred for 15 minutes. This was followed by addition of freshly-distilled cyclopentadiene (0.90 g, 0.91 ml, 8.5 mmol) by syringe. The reaction mixture was stirred at −78° C. and followed periodically by thin-layer-chromatography (using 66:34 ethylacetate:hexane) and deemed complete after 3 hours. The catalyst was then separated by filtration The product had an endo:exo ratio of 94:6. If it is desired, the reaction may be performed in the absence of the chiral bis(oxazoline) to yield a racemic mixture of the product.

EXAMPLE 3

Re-use of the Catalyst

The catalyst was recovered by filtration, filtered and washed with ethyl acetate (3×15 ml). It was then dried in a vacuum oven for 12 hours at 60° C. and then re-used following the same procedure as Example 2. The product was obtained at 78% yield and 70% ee. The endo:exo ratio was again 94:6. The results demonstrate that the catalyst may be re-used with maintained selectivity.

EXAMPLE 4

Use of Different Dienophiles and bis(imine) Ligands

The general method of Example 2 was repeated using cyclopentadiene as the diene with a range of different dienophiles as depicted in Table 2 below. The reaction times were varied as shown. In each case the copper-exchanged zeolite Y (CuHY) was treated with one of four different bis(oxazoline) compounds as follows;

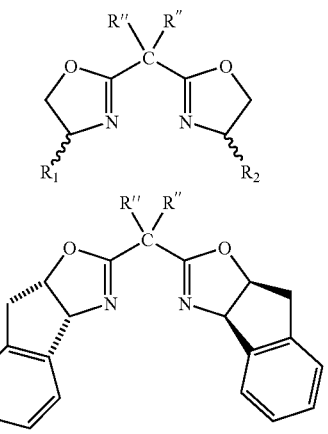

(1) R″ = CH$_3$; R$_1$ = R$_2$ = C$_6$H$_5$
(2) R″ = CH$_3$; R$_1$ = R$_2$ = C(CH$_3$)$_3$
(3) R″ = H; R$_1$ = R$_2$ = C(CH$_3$)$_3$
(4) R″ = CH$_3$

TABLE 2

| Example | Dienophile | Bisoxazoline/Catalyst | Product | Time (hrs) | Yield (%) | Ee (%) |
|---|---|---|---|---|---|---|
| 4a | Ph-CH=CH-C(O)-N(oxazolidinone) | 2/CuHY | Ph-norbornene-oxazolidinone adduct | 5 | 54 | 96 |
| 4b | EtO$_2$C-CH=CH-C(O)-N(oxazolidinone) | 2/CuHY | EtO$_2$C-norbornene-oxazolidinone adduct | 5 | 89 | 87 |
| 4c | Me-CH=CH-C(O)-N(oxazolidinone) | 2/CuHY | Me-norbornene-oxazolidinone adduct | 5 | 98 | 89 |
| 4d | CH$_2$=CH-C(O)-N(oxazolidinone) | 1/CuHY | norbornene-oxazolidinone adduct | 5 | 77 | 95 |
| 4e | CH$_2$=CH-C(O)-N(oxazolidinone) | 3/CuHY | norbornene-oxazolidinone adduct | 5 | 92 | 76 |
| 4f | CH$_2$=CH-C(O)-N(oxazolidinone) | 4/CuHY | norbornene-oxazolidinone adduct | 5 | 84 | 82 |
| 4g | CH$_2$=CH-SO$_2$Ph | 1/CuHY | cyclohexenyl-SO$_2$Ph | 25 | 45 | 71 |

TABLE 2-continued

| Example | Dienophile | Bisoxazoline/Catalyst | Product | Time (hrs) | Yield (%) | Ee (%) |
|---------|------------|----------------------|---------|------------|-----------|--------|
| 4h | (maleic anhydride) | 1/CuHY | (norbornene dicarboxylic anhydride adduct) | 3 | 92 | ND |
| 4i | (methylmaleic anhydride) | 1/CuHY | (Me-substituted norbornene anhydride adduct) | 4 | 91 | 91 |
| 4j | (methylenesuccinic anhydride) | 1/CuHY | (norbornene adduct with succinic anhydride) | 4 | 95 | 90 |

ND = not determined

EXAMPLE 5

Use of Different Dienes

The general method of Example 2 was repeated using cyclohexadiene or 2,3-dimethylbutadiene as the diene with the acrylamide dienophile depicted below. The reaction times were extended to 30 hours for these less active dienes. The copper-exchanged zeolite Y was treated in both cases with bis(oxazoline) compound (1). The results are given in Table 3;

TABLE 3

| Example | Diene | Dienophile | Product | Time (hrs) | Yield (%) | Ee (%) |
|---------|-------|------------|---------|------------|-----------|--------|
| 5a | (cyclohexadiene) | (Ph-CH=CH-C(O)-N-oxazolidinone) | (bicyclic Ph-substituted adduct) | 30 | 82 | 76 |
| 5b | (2,3-dimethylbutadiene) | (Ph-CH=CH-C(O)-N-oxazolidinone) | (dimethylcyclohexene Ph-substituted adduct) | 30 | 86 | 89 |

EXAMPLE 6

Use of Other Zeolitic Materials

The general method of Example 1 was repeated using ZSM-5. The resulting copper-exchanged ZSM-5 had a copper loading of 3.7% by weight.

Using the general method of Example 2, the copper-exchanged ZSM-5 was used for the reaction between cyclopentadiene and the acrylamide depicted below. The copper-exchanged ZSM-5 was treated with bis(oxazoline) compound (1). The result is given in Table 4;

TABLE 4

| Example | Dienophile | Bisoxazoline/Catalyst | Product | Time (hrs) | Yield (%) | Ee (%) |
|---|---|---|---|---|---|---|
| 6a | 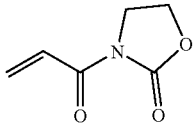 | 1/Cu ZSM-5 | 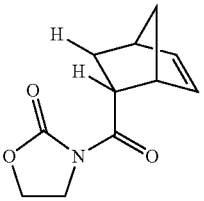 | 5 | 75 | 82 |

EXAMPLE 7

Hetero-Diels-Alder Reactions

The method of Example 2 was repeated using the Danisheffsky diene (7a, 7b) or cyclopentadiene (7c) as the diene with a range of different dienophiles as depicted in Table 7 below. The reaction times were extended accordingly to 30 or 48 hours. The catalysts comprised copper-exchanged zeolite Y treated with bis(oxazoline) (2). The results are given in Table 5;

TABLE 5

| Example | Dienophile | Bisoxazoline/Catalyst | Product | Time (hrs) | Yield (%) | Ee (%) |
|---|---|---|---|---|---|---|
| 7a | Ethyl glyoxylate | (2)/CuHY | 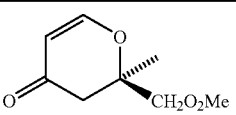 | 48 | 89 | 96 |
| 7b | o-Chlorobenzaldehyde | (2)/CuHY | 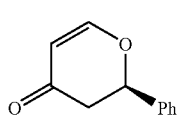 | 48 | 96 | 49 |
| 7c | 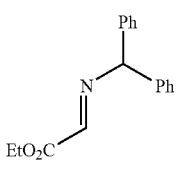 | (2)/CuHY | 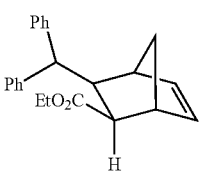 | 30 | 80 | 95 |

The invention claimed is:

1. A process for performing an enantioselective catalytic Hetero-Diels-Alder reaction by reacting a diene of formula (III) or (IV);

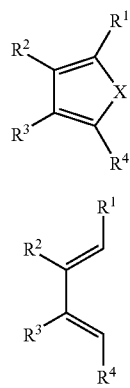

in which $R^1$, $R^2$, $R^3$, and $R^4$ are independently hydrogen, substituted or unsubtituted alkyl (C1-C12), cycloalkyl (C1-C12), aryl, alkoxy (C1-C12) and siloxy (C1-C12), halide, amino, amido, nitrile, thiol, sulphide, carbonyl, sulphonyl or phosphonyl; substituting groups being selected from the group consisting of alkyl, aryl, halide, alkoxy, amido, amino, nitrile, carbonyl and sulphonyl; X is $CH_2$, $C_2H_4$, $C_3H_6$, O, N (including N=N), S or P, which may be further substituted with hydrogen or a substituted or unsubstituted alkyl (C1-C12) or aryl group; or a cyclic diene comprising greater than one heteroatom selected from O, N or S in the ring structure; with a dienophile of formula (IX);

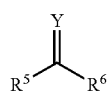

in which Y is O or NR, (where R is hydrogen, alkyl or aryl); $R^5$ and $R^6$ are independently hydrogen, alkyl (C1-C12), cycloalkyl (C1-C12), aryl, substituted aryl, ketone, aldehyde, ester, amide carboxylic acid, nitrile, nitrate, sulphonate or phosphonate, in the presence of a heterogeneous catalyst comprising zeolite Y or ZSM-5 with between 1 and 100% of the exchange sites occupied by copper ions, and a chiral bis(oxazoline) of formula (I) having an axis of symmetry through Z

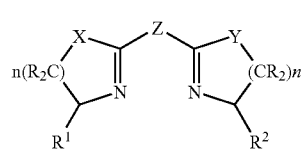

in which R=hydrogen, n=1, X and Y=O, Z=$CH_2$, $C(CH_3)_2$, $NCH_3$ or $1,5-C_6H_5N$ and $R^1$ and $R^2$ are the same and are alky (branched or linear C1-C10), cycloalkyl, aryl or benzyl which may be substituted or unsubstituted; substituting groups being selected from the group consisting of halogen, hydroxyl, carboxyl, amide, silyl and aryl.

2. The process according to claim 1 wherein the catalyst contains 0.1 to 15% by weight of copper.

3. The process according to claim 1 wherein between 0.40 and 0.80 molar equivalents of chiral bis(oxazoline) are present per copper ion.

4. The process according to claim 1 wherein the chiral bis(oxazoline) is selected from the group consisting of a (S,S)-bis(tert-butyloxazoline), (R,R)-bis(phenyloxazoline), (S,S)bis(phenyloxazoline), (R,R)-bis(benzyloxazoline) and 2,2-bis(8,8'-dihydro-3aH-indeno[1,2-d]oxazol-2-yl)propane.

5. The process according to claim 1 wherein the diene is substituted or unsubstituted cyclopentadiene, furan, pyrrole, oxazole or thiophene, or the Danishefsky diene or the Brassart diene.

6. The process according to claim 1 wherein the reaction is effected at a temperature in the range –80° C. to +80° C.

7. The process according to claim 1 wherein the amount of catalyst used provides between 0.01 and 0.5 moles of copper per mole of dienophile.

8. The process according to claim 1 wherein upon completion of the reaction, the catalyst is separated from the reation mixture and re-used.

9. The process according to claim 1 wherein in the chiral bis(oxazoline) of formula (I), $R^1$ and $R^2$ are selected from the group consisting of tert-butyl, isopropyl, phenyl and benzyl.

10. A process according to claim 1 wherein in the dienophile of formula (IX) $R^5$=$R^6$=$CO_2R'$, wherein R' is C1-C12 alkyl.

* * * * *

UNITED STATES PATENT AND TRADEMARK OFFICE
CERTIFICATE OF CORRECTION

PATENT NO. : 7,262,299 B2  Page 1 of 1
APPLICATION NO. : 10/495004
DATED : August 28, 2007
INVENTOR(S) : Neil Aubrey Caplan et al.

It is certified that error appears in the above-identified patent and that said Letters Patent is hereby corrected as shown below:

At column 20, line 15, "alky" should read --alkyl--.

At column 20, line 28, "(S,S)bis(phenyloxazoline)" should read --(S,S)-bis(phenyloxazoline--.

Signed and Sealed this

Seventeenth Day of June, 2008

JON W. DUDAS
*Director of the United States Patent and Trademark Office*